United States Patent [19]

Yoshioka et al.

[11] Patent Number: 5,149,802

[45] Date of Patent: Sep. 22, 1992

[54] PROCESS FOR PRODUCING AZETIDINONE DERIVATIVES

[75] Inventors: Takeo Yoshioka, Ayase; Ryoichi Miyata, Fujisawa; Toshio Tsuchida; Hiroshi Tone, both of Yokohama; Rokuro Okamoto, Fujisawa, all of Japan

[73] Assignee: Mercian Corporation, Tokyo, Japan

[21] Appl. No.: 729,771

[22] Filed: Jul. 10, 1991

Related U.S. Application Data

[62] Division of Ser. No. 599,354, Oct. 5, 1990, abandoned.

[30] Foreign Application Priority Data

Oct. 6, 1989 [JP] Japan .................................. 1-260278

[51] Int. Cl.$^5$ .................... C07D 205/08; C07D 405/04
[52] U.S. Cl. ...................................................... 540/200
[58] Field of Search ......................................... 540/200

[56] References Cited

U.S. PATENT DOCUMENTS

| | | | |
|---|---|---|---|
| 3,717,647 | 2/1973 | Villani | 546/346 |
| 4,000,283 | 12/1976 | Jarque | 546/343 |
| 4,214,101 | 7/1980 | Miya | 562/421 |
| 4,238,625 | 12/1980 | Fiege | 562/421 |
| 4,287,123 | 9/1981 | Liu et al. | |
| 4,976,893 | 12/1990 | Leupold | 562/421 |

FOREIGN PATENT DOCUMENTS

| | | |
|---|---|---|
| 0032400 | 7/1981 | European Pat. Off. |
| 0146735 | 11/1984 | European Pat. Off. |
| 160876 | 11/1985 | European Pat. Off. ............ 540/350 |
| 63-04656 | 6/1988 | Japan |
| PCT/JP87/0-0991 | 1/1987 | PCT Int'l Appl. |

OTHER PUBLICATIONS

Green, "Protective Groups in Organic Chemistry", (1981) pp. 10–12.
Lavock, "Comprehensive Organic Transformations" (1989), pp. 353–358.
Heyns, Chem. Ber. 89, 1648 (1956).
Yoshida, Tetrahedron Letters, vol. 25, No. 26, pp. 2793–2796, 1984.
Melillo, Tetrahedron Letters, vol. 21, pp. 2783–2786, 1980.

Primary Examiner—Mark L. Berch
Attorney, Agent, or Firm—Wenderoth, Lind & Ponack

[57] ABSTRACT

A process for producing 2-azetidinone derivatives represented by formula

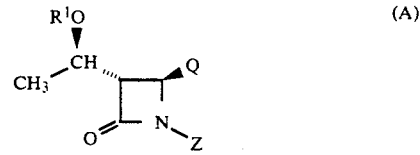

(A)

wherein
$R^1$ denotes a protecting group of a hydroxyl group,
Z denotes a hydrogen atom or a protecting group of an amino group, and
Q denotes

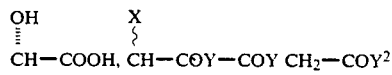

in which X denotes a halogen atom, Y denotes a halogen atom or $OR^2$, $R^2$ denotes a hydrogen atom or a protecting group of a carboxyl group, and $Y^2$ denotes $OR^3$ or $SR^4$ in which $R^3$ denotes a hydrogen atom, a protecting group of a carboxyl group or an ester residue and $R^4$ denotes an ester residue.

1 Claim, No Drawings

PROCESS FOR PRODUCING AZETIDINONE DERIVATIVES

This application is a division of now abandoned Ser. No. 07,599,354 filed Oct. 5, 1990 ABN.

This invention relates to a process for producing 2-azetidinone derivatives. More specifically, this invention relates to a process for produing 2-azetidinnoe derivatives represented by formula

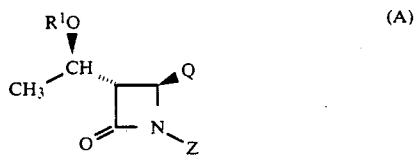

wherein
$R^1$ denotes a protecting group of a hydroxyl group
Z denotes a hydrogen atom or a protecting group of an amino group, and
Q denotes $$CH-COOH, \quad CH-COY-COY \quad CH_2-COY^2$$
with OH, X substituents in which X denotes a halogen atom, Y denotes a halogen atom or $OR^2$, $R^2$ denotes a hydrogen atom or a protecting group of a carboxyl group, and $Y^2$ denotes $OR^3$ or $SR^4$ in which $R^3$ denotes a hydrogen atom, a protecting group of a carboxyl group or an ester residue and $R^4$ denotes an ester residue.

The compounds represented by formula (A) are, as will be later described, useful as intermediates for synthesis of imipenem antibiotics or carbapenem antibiotics having excellent antibacterial activity, such as RS-533, etc.

Several methods for producing the compounds represented by formula (A) have been proposed (see, for example, U.S. Pat. No. 4,287,123 and CH 6286/83-1). However, the prior processes suffered drawbacks that many steps are required, costly reagents are needed and the reaction operation is complex; thus none were industrially fully satisfactory.

This invention is to provide a novel, useful process for producing compounds represented by the above formula (A). The process is schematically shown below.

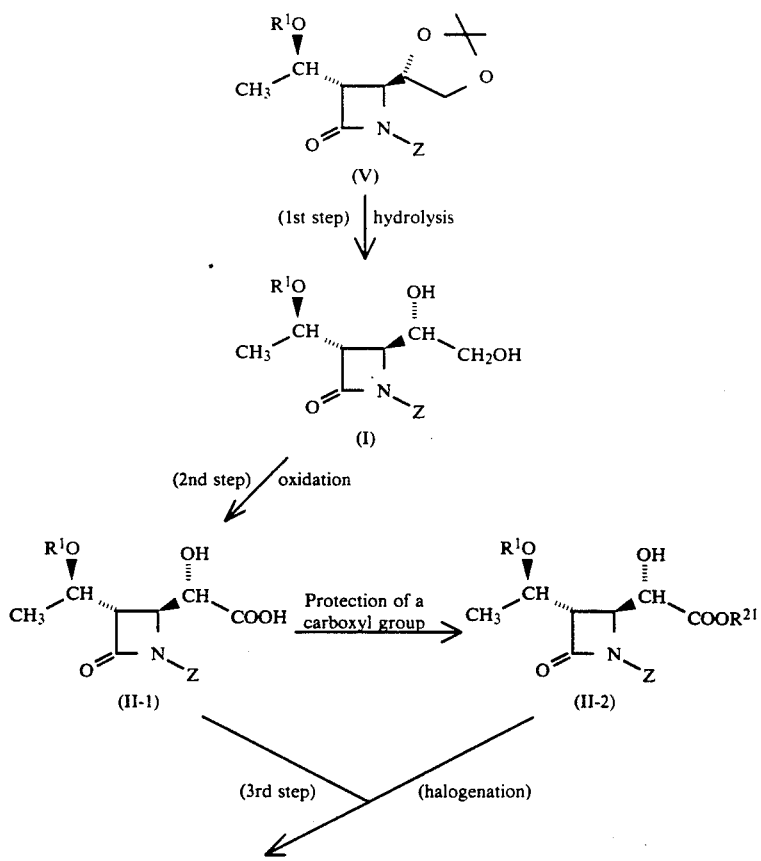

Reaction Scheme 1

Reaction Scheme 1

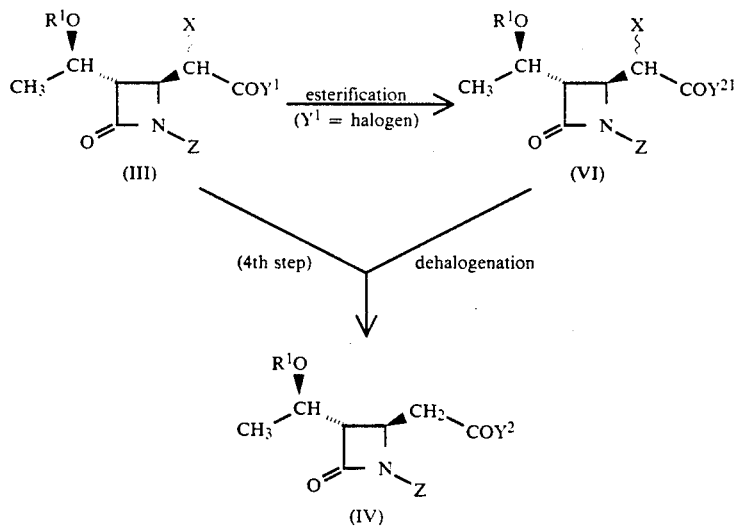

In the above reaction formula (I),
$R^1$ denotes a protecting group of a hydroxyl group,
Z denotes a hydrogen atom or a protecting group of an amino group,
$R^{21}$ denotes a protecting group of a carboxyl group,
X denotes a halogen atom,
$Y^1$ denotes a halogen atom or $OR^2$ in which $R^2$ denotes a hydrogen atom or a protecting group of a carboxyl group,
$Y^{21}$ denotes $OR^{31}$ or $SR^4$ in which $R^{31}$ and $R^4$ each denote an ester residue, and
$Y^2$ denotes $OR^3$ or $SR^4$ in which $R^3$ denotes a hydrogen atom, a protecting group of a carboxyl group or an ester residue.

In this invention, The "protecting gorup of a hydroxyl group" is an ordinary protecting group of a hydroxy group that can be elminated by hydrolysis or hydrogenolysis. Examples thereof are as follows.

(1) lower alkanoyl group: acetyl, propionyl and butyryl
(2) halo-lower alkyl group: chloroacetyl, dichloroacetyl, trichloroacetyl, bromoacetyl and dibromoacetyl
(3) substituted or unsubstituted allyl group: allyl and 2-methylally
(4) substituted or unsubstituted benzyl group: benzyl, p-methoxybenzyl, p-nitrobenzykl, p-methylbenzyl, p-chlorobenzyl and o,p-dinitrobenzyl
(5) substituted or unsubstituted benzyloxycarbonyl group: benzyloxycarbonyl p-nitrobenzyloxycarbonyl and p-chlorobenzyloxycarbonyl The "protecting group of an amino group" can be any usual protecting group of an amino group known in the field of. a peptide chemistry. Typical examples thereof are as follows.

(1) substituted or unsubstituted phenyl group: 4-methoxyphenyl and 2,4-dimethoxyphenyl substituted or unsubstituted aralkyl group: benzyl, p-nitrobenzyl, dianisylmethyl and 2,4-dimethoxybenzyl The "protecting group of a carboxyl group" may be any ordinary protecting group of a carboxyl group that can be eliminated by hydrolysis or hydrogenolysis. Typical examples thereof are as follows.

(1) lower alkyl group: methyl, ethyl, propyl, butyl or tert-butyl
(2) substituted or unsubstituted benzyl: benzyl, p-methoxybenzyl, p-nitrobenzyl: p-chlorobenzyl, p-methylbenzyl or o,p-dinitrobenzyl Examples of the "halogen atom" include fluorine, chlorine, bromine and iodine atoms. Examples of the "ester residue" include an alkyl group such as methyl, ethyl, propyl, butyl or tert-butyl; a substituted or unsubstituted benzyl group such as benzyl, p-methoxybenzyl, p-nitrobenzyl, p-chlorobenzyl, p-methylbenzyl or o,p-dinitrobenzyl: and a phenyl group.

The word "lower" referred to in this invention means that the number of carbon atoms of an atomic group or a compound modified by this word is not more than 6, preferably not more than 4.

The respective steps in the reaction scheme 1 will be explained in more detail below.

1st Step

In the 1st step, the known compound of formula (V) is hydrolyzed into the compound of formula (I) according to PCT/JP 87/00991.

The hydrolysis of the compound of formula (V) can be carrier out with an acid in an aqueous medium under the usual conditions. Examples of the acid are organic acids such as acetic acid and trifluoroacetic acid; and inorganic acids such as hydrochloric acid, sulfuric acid and sulfonic acid.

As a result, the protecting group of the diol in the side chain at the 4-position of the component of formula (V) is elminated to obtain the compound of formula (I).

2nd step

The compound of formula (I) obtained in the 1st step is then oxidized into the compound of formula (II-I).

The oxidation is conducted with an oxygen-containing gas in the presence of a catalyst. The oxygen-containing gas is an oxygen gas, air or a mixture of the oxygen gas and an inert gas. Among them, air is preferable. The catalyst is, for example, a platinum-type catalyst such as a platinum-supported carbon or platinum black.

The oxidation is usually carried out by dissolving or dispersing the compound of formula (I) in a solvent such as water, a buffer solution (e.g. a phosphoric acid buffer solution) or an alcohol, and blowing the oxygen-containing gas at a temperature of about 20° to about 100° C., preferably about 70 to about 90° C. On that occasion, pH of the reaction liquid is kept within the range of about 7 to 9, preferably 8 to 9 (neutrality or weak alkalinity). To this end, a basic compound such as sodium bicarbonate, sodium carbonate or sodium hydroxide may be added to adjust the pH.

The above oxidation reaction can be usually effected under normal pressure, and if required, under elevated pressure or under reduced pressure.

The reaction can usually continue for 5 to 20 hours under such conditions.

In the thus obtained compound of formula (II-I), the carboxyl group in the side chain at the 4-position may be protected if required. The protection of the carboxyl group can be carried out by a method known per se which is suited for the protecting group according to the type of the protecting group. Examples of said method include a method of a reaction with diazomethane or diazophenylmethane, a method of a reaction with an alkyl iodide or benzyl bromide in the presence of anhydrous dimethylformamide, and a method of a reaction with a dehydrocondensation agent such as dicyclohexylcarbodiimide in the presence of an alcohol. Thus, the compound of formual (II-2) is afforded.

3rd step

In the 3rd step, the compound of the formula (II-1) or (II-2), i.e. the compound represented by formula

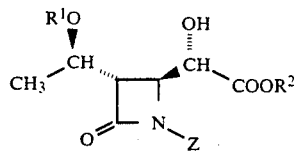

(II)

wherein $R^1$, $R^2$ and $Z$ are defined above, is halogenated to form the compound of formula (III).

The halogenation can be conducted by reacting the compound of formula (II) with the halogenating agent. The halogenating agent can be an agent ordinarily used to replace an alcoholic hydroxyl group with a halogen atom. Examples of the halogenating agent are thionyl chloride, thionyl bromide, phosphorus pentachloride, phosphorus oxychloride and oxalyl chloride.

The halogenation can ordinarily be carried out in a suitable solvent at a temperature of about −30° C. to a reflux temperature of a solvent, preferably about 20° to about 70° C. Examples of the solvent are aromatic hydrocarbons such as toluene and benzene; halogenated hydrocarbons such as dichloromethane, chloroform and carbon tetrachloride; and esters such as ethyl acetate.

The amount of the halogenating agent cannot strictly be limited, but usually 1 to 10 equivalents, preferably 2 to 5 equivalents per mol of the compound of formula (II).

Thus, the halogen atom introduced on the carbon atom adjacent the 4-position of the azetidinone ring provides a S- or R-steric configuration, or a combination or them according to the type of the halogenating agent.

When $Y^1$ is a halogen atom in the resulting compound of formula (III), said compund can be esterified into the compuond of formula (VI), if required, by the reaction with an alcohol or a thiol represented by formula $$Y^{21}H \qquad (VII)$$

wherein $Y^{21}$ is as defined above.

The esterification can be carried out in a usual manner. For example, it can be effected in a suitable solvent at a temperature of about −30° C. to a reflux temperature of a solvent, preferably about 0 to about 30° C. Examples of the solvent are aromatic hydrocarbons such as benzene and toluene; halogenated hydrocarbons such as chloroform and dichloromethane; esters such as hydrofuran (THF); dimethylformamide (DMF); and pyridine.

The amount of the alcohol or the thiol of formula (VII) is not particularly limited, but usually 1 to 100 mols, preferably 1 to 10 mols per mol of the compound of formula (III) ($Y^1$=halogen atom).

4step

In the 4step, the compound of formula (III) or (VI) obtained in the 3rd step, i.e. the compound represented by formula

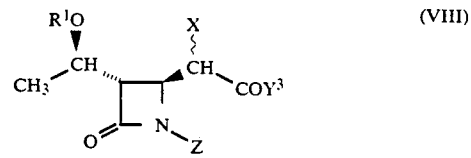

(VIII)

wherein $Y^3$ denotes $Y^1$ or $Y^{21}$, and $R^1$, $Z$, $X$, $Y^1$ is subjected to a dehalogenation reaction to form the compound of formula (IV).

By the dehalogenation, the halogen atom can reductively by eliminated by catalytic reduction of the compound of formula (VIII) or reduction thereof with a metal and an acid, e.g. a Zn-acetic acid system. Examples of the solvent ordinarily used in the reductive dehalogenation are acetic acid; and water, methanol, ethanol, ethyl acetate, dichloromethane and DMF, either singly or in combination with acetic acid.

Especially when the reductive dehalogenation of the compound of formula (VIII) with $Y^3$=halogen atom is performed in a solvent such as water, an alcohol of formula $R^{31}OH$ or a thiol of formula $R^4SH$, there results not the compound of formula (IV) wherein $Y^2$ is a halogen atom, but the compound of formula (IV) wherein $Y^2$ is a hydroxyl group, $OR^{31}$ or $OR^4$.

When the compound of formula (VIII) with $Y^3$=halogen atom is reductively dehalogenated without using the solvent, a mixed acid anhydride is formed as an intermediate. When this is washed with water, hydrolysis easily occurs, and the compound of formula (IV) with $Y^2$=hydroxyl group is obtained.

The reductive dehalogenation of the compound of formula (VIII) can be carried out with a zinc powder dispersed in a medium of an acetic acid at a temperature of usually −30° to 50° C., preferably 0° to 25° C. At this time, the amount of the zinc powder is 1 to 100 equivalents, preferably 5 to 80 equivalents based on the halogenated compound of formula (VIII).

The above obtained compound of formula (IV) can be separated from the reaction mixture and/or purified by a suitable combination of crystallization, chromatography, extraction and filtration.

The compound of formula (IV) produced by the process of this invention is useful as, for example, an intermediate of carbapenem antibiotic. For instance, the compound of formula (IV) with $Y^2$=hydroxyl group can be, after eliminating the protecting group ($R^1$) of the hydroxyl group by alkaline hydrolysis or hydrogenolysis, formed into carbapenem represented by formula

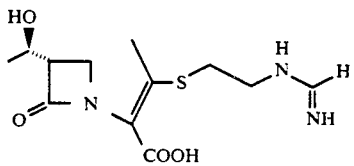

through a method described in D. G,. Melillo, I. Shinkai, et al. Tetrahdron Letters, 21, 2783.

The compound of formula (IV) with $Y^2$=S-phenyl group can be formed into RS-533 represented by formula

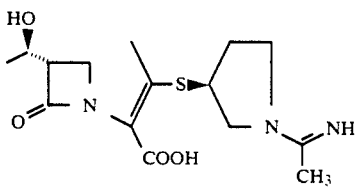

via a method described in EP 102239.

In the aforesaid process of this invention, the compound of formula (VIII) obtained in the 3rd step, especially a compound represented by formula

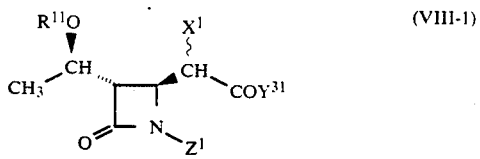

wherein
$R^{11}$ denotes a lower alkanoyl group such as acetyl, propionyl, chloroacetyl or bromoacetyl, a halo-lower alkanoyl group such as chloroacetyl, trichloroacetyl or bromoacetyl, an allyl group, a substituted or unsubstituted benzyl group such as benzyl, p-methoxybenzyl or p-nitrobenzyl, or a substituted or unsubstituted benzyloxycarbonyl group such as benzyloxycarbonyl or- p-nitrobenzyloxycarbonyl, $X^1$ denotes a chlorine atom or a bromine atom, $Y^{31}$ denotes a chlorine atom, a bromine atom, $OR^{32}$, a -S-lower alkyl group or a -S-phenyl group in which $R^{32}$ denotes a hydrogen atom, a lower alkyl group such as methyl, ethyl, propyl or butyl, or a substituted or unsubstituted benzyl group such as benzyl, p-nitrobenzyl, p-methyl benzyl or p-chlorobenzyl, $Z^1$ denotes a hydrogen atom, a substituted or unsubstituted phenyl group such as p-methoxyphenyl or o,p-dimethyoxyphenyl, or a substituted or unsubstituted aralkyl group such as benzyl, p-nitrobenzyl or dianisylmethyl, is a novel compound undescribed in the prior literature. Typical examples thereof are tabulated below.

| Compound | $R^{11}$ | $X^1$ | $Y^{31}$ | $Z^1$ |
|---|---|---|---|---|
| 1 | COCH₃ | Cl | OCH₃ | ⟨phenyl⟩-OCH₃ |
| 2 | COCH₃ | Br | OCH₃ | ⟨phenyl⟩-OCH₃ |
| 3 | COCH₃ | Cl | S-⟨phenyl⟩ | ⟨phenyl⟩-OCH₃ |
| 4 | COCH₃ | Cl | OCH₂-⟨phenyl⟩ | ⟨phenyl⟩-OCH₃ |

-continued
(VIII-1)
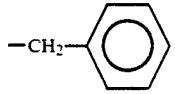
| Compound | R¹¹ | X¹ | Y³¹ | Z¹ |
|---|---|---|---|---|
| 5 | COCH₂CH₃ | Cl | OCH₂CH₃ | —CH₂—C₆H₅ |
| 6 | COCH₃ | Cl | OCH₃ | 2,4-(OCH₃)₂C₆H₃— |
| 7 | —CH₂—C₆H₅ | Cl | OCH₃ | 4-CH₃O—C₆H₄— |
| 8 | —CH₂—C₆H₅ | Cl | OCH₂—C₆H₅ | 4-CH₃O—C₆H₄— |
| 9 | —CH₂—C₆H₅ | Cl | —S—C₆H₅ | 4-CH₃O—C₆H₄— |
| 10 | —CH₂—C₆H₅ | Cl | OCH₃—C₆H₄— | —CH(4-CH₃O—C₆H₄)₂ |
| 11 | —CH₂—C₆H₅ | Cl | OCH₂—C₆H₅ | —CH(4-CH₃O—C₆H₄)₂ |
| 12 | —CH₂—C₆H₅ | Cl | —S—C₆H₅ | —CH(4-CH₃O—C₆H₄)₂ |
| 13 | —CH₂—C₆H₅ | Cl | OCH₃ | 2,4-(OCH₃)₂C₆H₃— |

-continued

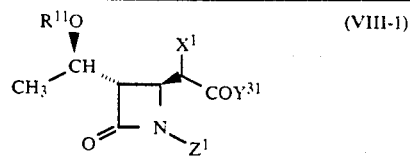
(VIII-1)

| Compound | R¹¹ | X¹ Y³¹ | Z¹ |
|---|---|---|---|
| 14 | CH₂-C₆H₅ (benzyl) | Cl, OCH₂-C₆H₅ | 2,4-dimethoxyphenyl (OCH₃, OCH₃) |
| 15 | CH₂-C₆H₅ | Cl, -S-C₆H₅ | 2,4-dimethoxyphenyl |
| 16 | CH₂-C₆H₅ | Br, OCH₂-C₆H₅ | 4-OCH₃-phenyl |
| 17 | CH₂-C₆H₅ | Cl, OCH₂-C₆H₅ | -CH₂-C₆H₅ |
| 18 | CH₂-C₆H₅ | Cl OCH₂CH₃ | 4-OCH₃-phenyl |
| 19 | CH₂-C₆H₄-OCH₃ | Cl, OCH₂-C₆H₅ | 4-OCH₃-phenyl |
| 20 | CH₂-C₆H₄-OCH₃ | Cl OCH₃ | 4-OCH₃-phenyl |
| 21 | CH₂-C₆H₄-OCH₃ | Cl, S-C₆H₅ | 4-OCH₃-phenyl |
| 22 | CH₂-C₆H₄-OCH₃ | Cl, OCH₂-C₆H₅ | 2,4-dimethoxyphenyl |
| 23 | CH₂-C₆H₄-OCH₃ | Cl OCH₃ | 2,4-dimethoxyphenyl |
| 24 | CH₂-C₆H₄-OCH₃ | Cl, S-C₆H₅ | 2,4-dimethoxyphenyl |

-continued (VIII-1)

| Compound | R¹¹ | X¹ | Y³¹ | Z¹ |
|---|---|---|---|---|
| 25 | CH₂-C₆H₄-OCH₃ (p) | Cl | OCH₂-C₆H₅ | -CH(C₆H₄-OCH₃ (p))₂ |
| 26 | CH₂-C₆H₄-OCH₃ (p) | Cl | OCH₃-C₆H₅ | -CH(C₆H₄-OCH₃ (p))₂ |
| 27 | CH₂-C₆H₄-OCH₃ (p) | Cl | S-C₆H₅ | -CH(C₆H₄-OCH₃ (p))₂ |
| 28 | CH₂-C₆H₄-NO₂ (p) | Cl | OCH₂-C₆H₅ | -C₆H₄-OCH₃ (p) |
| 29 | CH₂-C₆H₄-NO₂ (p) | Cl | OCH₃ | -C₆H₄-OCH₃ (p) |
| 30 | CH₂-C₆H₄-NO₂ (p) | Cl | S-C₆H₅ | -C₆H₄-OCH₃ (p) |
| 31 | CH₂-C₆H₅ | Cl | OCH₂-C₆H₄-NO₂ (p) | -C₆H₄-OCH₃ (p) |
| 32 | COCH₃ | Cl | OCH₂-C₆H₄-NO₂ (p) | -C₆H₄-OCH₃ (p) |
| 33 | COOCH₂-C₆H₅ | Cl | OCH₂-C₆H₅ | -C₆H₄-OCH₃ (p) |

-continued

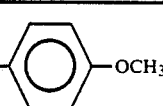

(VIII-1)

| Compound | R¹¹ | X¹ | Y³¹ | Z¹ |
|---|---|---|---|---|
| 34 | CH₂–⟨phenyl⟩ | Cl | OCH₂–⟨phenyl⟩–Cl | –⟨phenyl⟩–OCH₃ |
| 35 | CH₂–⟨phenyl⟩ | Cl | OCH₂–⟨phenyl⟩–CH₃ | –⟨phenyl⟩–OCH₃ |
| 36 | COOCH₂–⟨phenyl⟩–NO₂ | Cl | OCH₂–⟨phenyl⟩ | –⟨phenyl⟩–OCH₃ |

The following Examples illustrate this invention more specifically.

EXAMPLE 1

Synthesis of (3S,4S)-3-[(1R)-1-acetoxyethyl]-4-[(S)-2,2-dimethyl-1,3-dioxolan-4-yl]-1-(4-methoxy)phenyl-2-azetidinone 3

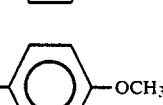

One hundred milligrams (0.3085 mmol) of compound 1 was dissolved in 0.5 ml of pyridine, and 43.7 microliters (0.4627 mmol) of acetic anhydride was added dropwise under ice cooling, followed by stirring overnight at room temperature. The reaction mixture was poured into ice water and extracted with ethyl acetate. The organic layer was washed twice with 0.1 N hydrochloric acid and twice with a saturated sodium chloride aqueous solution, and then dehydrated with anhydrous sodium sulfate. The resulting product was concentrated to dryness under reduced pressure and purified by silica gel column chromatography (Merck Art 7734, (1) toluene, (2) toluene/ethyl acetate=10:1, (3) 7:1, (4) 5:1, (5) 3:1, (6) 2:1) to obtain 107.9 mg of the captioned compound (yield 96%).

White needle crystal.

m.p.: 117°–119.5° C..

IR(CHCl₃); 1730 cm⁻¹(β-lactam C=O), 1725 cm⁻¹(ester C=O), 1510 cm⁻¹(p-methoxyphenyl).

NMR(CDCl₃)δ(PPM): 1.33(3H, s, CH₃), 1.40(3H, s, CH₃), 1.44(3H, d, J=6.0 Hz, CH₃).

$$2.05(3H, s, \overset{O}{\overset{\parallel}{C}}CH_3)$$

3.31(1H, dd, J=1.5, 7.5 Hz, CH-3), 3.81(3H, s, OCH₃), 3.67–3.87(1H, m, CH-6), 4.01–4.20(2H, m, CH-6, CH-4), 4.49(1H, dt, J=3.9, 7.5 Hz, CH-5), 5.12–5.42(1H, m, CH-7)

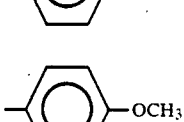

6.88(2H, d, J=9Hz, ⟨phenyl⟩–OCH₃)

7.36(2H, d, J=9Hz, ⟨phenyl⟩–OCH₃)

EXAMPLE 2

Synthesis of (3S,4S)-3-[(1R)-1-acetoxyethyl]-4-[(S)-1,2-dihydroxyethyl]-1-(4-methoxy)phenyl-2-azetidinone 4

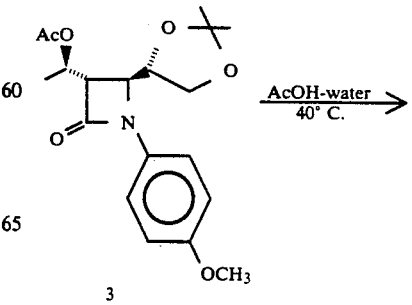

-continued

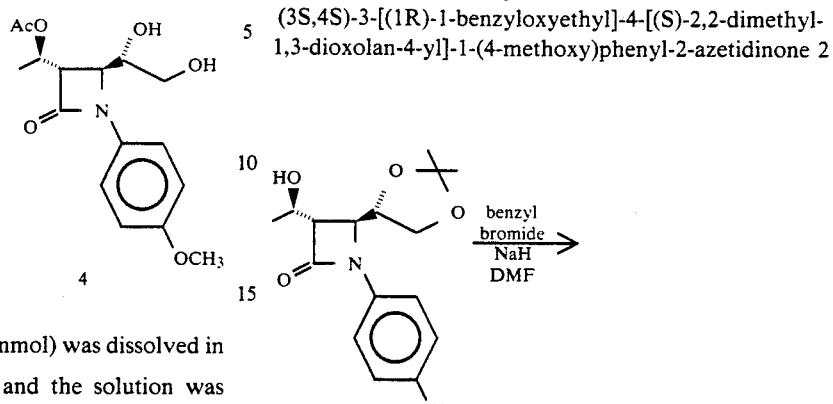

Compound 3 (52.8 mg: 0.1442 mmol) was dissolved in 1 ml of acetic acid-water (4:1) and the solution was stirred at 40° C. for 22 hours. Toluene was added to the reaction solution and the mixture was concentrated to dryness under reduced pressure. The residue was purified by silica gel column chromatography (Merck ARt 7734, (1) toluene, (2) toluene/ethyl acetate=5:1, (3) 3:1, (4) 2:1, (5) 1:2, (6) 1:3) to afford 43.4 mg of the captioned compound as an oil (yield 98%).

IR(CHCl₃); 1740 cm⁻¹(β-lactam C=O), 1510 cm⁻¹(p-methoxyphenyl.

NMR(CDCl₃)δ(PP,):

1.40(3H, d, J=6.0 Hz, CH₃),

2.02(3H, s, CCH₃)

2.76(1H, bt, J=6 Hz, CH-5), 3.10(1H, bd, J=4.5 Hz, CH-6), 3.48(1H, dd, J=1.5 Hz, 7.5 Hz, CH-3), 3.80(3H, s, CCH₃), 3.53-3.73(2H, m, CH₂-6), 4.05(1H, t, J=1.5 Hz, CH-4), 4.13-4.33(1H, m, CH-7), 5.27(1H, m, CH-5),

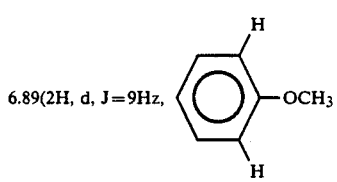
6.89(2H, d, J=9Hz,

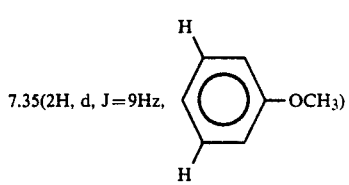
7.35(2H, d, J=9Hz,

EXAMPLE 3

Synthesis of (3S,4S)-3-[(1R)-1-benzyloxyethyl]-4-[(S)-2,2-dimethyl-1,3-dioxolan-4-yl]-1-(4-methoxy)phenyl-2-azetidinone 2

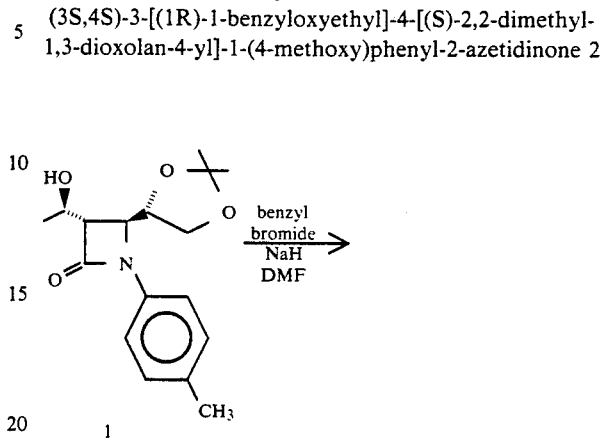

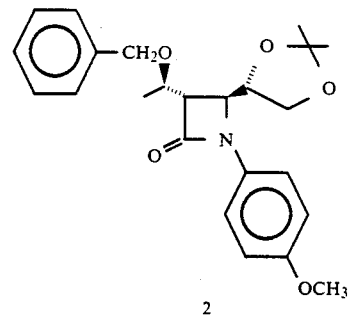

Two grams (6.223 mmols) of compound 1 was dissolved in 40 ml of anhydrous DMF, and 280 mg (7.0 mmols) of NaH was added under ice cooling, After stirring for 5 minutes, 1.12 ml (9.71 ml) of benzyl bromide was added dropwise. The mixture was stirred overnight at room temperature, and 200 ml of acetic acid was then added. The reaction mixture was washed with 100 ml of a 15% sodium chloride aqueous solution and then with 50 ml of a saturated sodium chloride aqueous solution. Subsequently, the resulting product was dehydrated with anhydrous sodium sulfate and concentrated to dryness under reduced pressure.

The residue was purified by silica gel column chromatography (Merck Art 7734, (1) toluene, (2) toluene/ethyl acetate=10:1) to obtain 2.46 g of the captioned compound (yield 96.1%).

White crystal. m.p.: 109°-111° C.

IR(CHCl₃(; 1735 cm¹(β-lactam C=O), 1510 cm¹(p-methoxyphenyl).

NMR(CDCl₃)δ(PPM):

1.31(3H, s, H₃C⨯CH₃)

1.39(3H, s, H₃C⨯CH₃)

1.40(3H, d, J=6.0 Hz, CH₃), 3.22(1H, dd, J=2.2, 7.2 Hz, CH-3), 3.80(3H, s, OCH₃), 3.80-4.2(4H, m, CH-4, CH-7, CH₂-6)

4.4–4.7(3H, m, C6H5-CH2, CH-5) 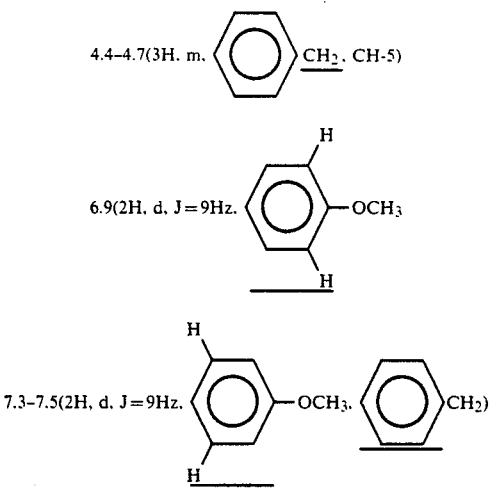

6.9(2H, d, J=9Hz, C6H4-OCH3)

7.3–7.5(2H, d, J=9Hz, C6H4-OCH3, C6H5-CH2)

4.56(2H, AB1, C6H5-CH2) 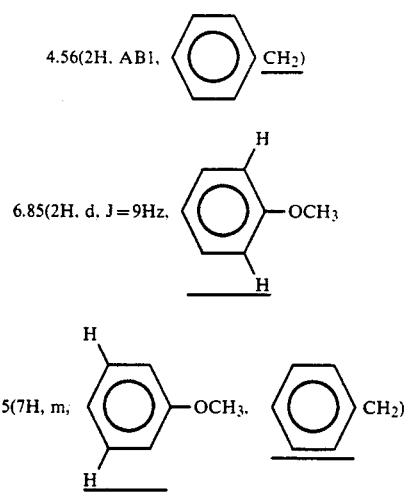

6.85(2H, d, J=9Hz, C6H4-OCH3)

7.25–7.5(7H, m, C6H4-OCH3, C6H5-CH2)

EXAMPLE 4

Synthesis of (3S,4S)-3-[(1R)-1-benzyloxyethyl]-4-[(1S)-1,2-dihydroxyethyl]-1-(4-methoxy) phenyl-2-azetidinone 4

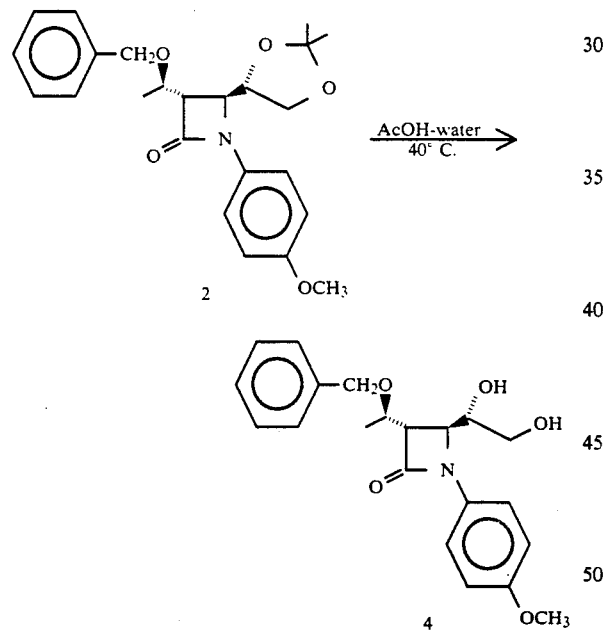

Compound 2 (2.4 g: 5.832 mmols) was dissolved in 130 ml of acetic acid-water (4:1) and the solution was stirred at 40° C. for 14 hours. The reaction mixture was concentrated to dryness under reduced pressure. The residue was purified by silica gel column chromatography (Merck Art 7734 (1) toluene, (2) toluene:ethyl acetate=3:1, (3) toluene:ethyl acetate=1:1) to obtain 2.1 g of IR(CHCl3); 1730 cm$^{-1}$(β-lactam C=O), 1510 cm$^{-1}$(p-methoxyphenyl), NMR(CDCl3)δ(PPM): 1.40(3H, d, J=6.0 Hz, CH3), 2.85(1H, bd, J=5.0 Hz, OH-5), 3.08(1H, bt, J=7.0 Hz, OH-6), 3.42(2H, dd, J=2.0, 9.1 Hz, CH-3), 3.80(2H, m, CH2-6), 3.22(1H, dd, J=2.2, 7.2 Hz, CH-3), 3.80(3H, s, OCH3), 3.85–4.20(3H, m, CH-4, CH-5, CH-7).

EXAMPLE 5

Synthesis of (3S,4S)-3-[(1R)-1-benzyloxyethyl]-4-[(1S)-1-hydroxy-1-carboxy]methyl]-1-(4-methoxy)phenyl-2azetidinone 6

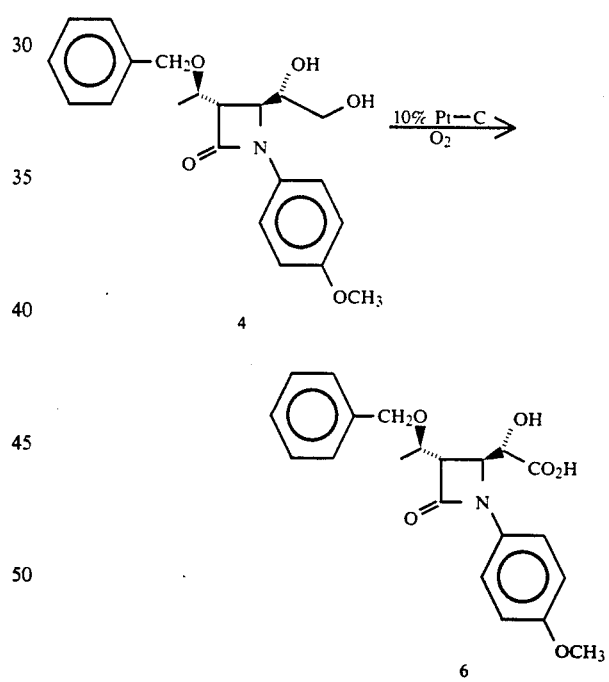

One gram (2.692 mmols) of compound 4 was dissolved in 20 ml of isopropyl alcohol, and 40 ml of 0.1 M PBS with pH of 8.0 was added. Further, 670 mg of 10% Pt-C was added, and air was blown while stirring the mixture at 80° to 85° C.

After stirring for 14 hours, the reaction mixture was cooled and filtered though celite, followed by washing with 0.1 M PBS. After the filtrate and the washing were together with dichloromethqane, the aqueous layer was adjusted to pH of 2.5 with 1N HCl and extracted with 100 ml and 50 ml of dichloromethane. The extract was washed with a saturated sodium chloride aqueous solution, then dehydrated with anhydrous sodium sulfate and concentrated to dryness under reduced pressure to obtain 830 mg of the captioned compound (yield 80%).

IR(CHCl$_3$); 1730 cm$^{-1}$($\beta$-lactam C=O), 1510 cm$^{-1}$.

NMR(CDCl$_3$)$\delta$(PPM): 1.21(3H, d, J=6.2 Hz, CH$_3$), 3.44(1H, dd, J=2.0 Hz, 3.8 Hz, CH-3), 3.76(3H, s, OCH$_3$), 3.95(1H, m, CH-7), 3.80(2H, m, CH$_2$-6),

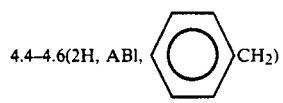
4.4–4.6(2H, ABl, 4.73(1H, d, J=2.0 Hz, CH-5),

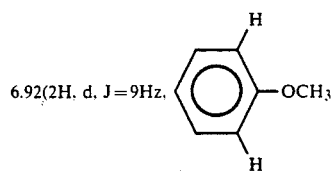
6.92(2H, d, J=9Hz,

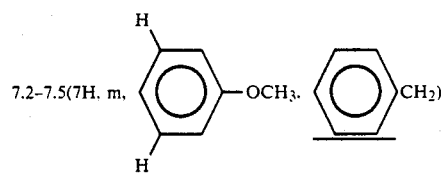
7.2–7.5(7H, m,

EXAMPLE 6

Synthesis of 3S,4S)-3-[(1R)-1-benzyloxyethyl]-4[(1S)-1-hydroxy-1-benzyloxycarbonyl)methyl]-1-(4-methoxy)phenyl-2-azetidinone 7

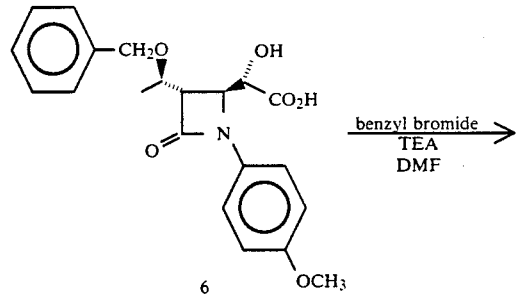

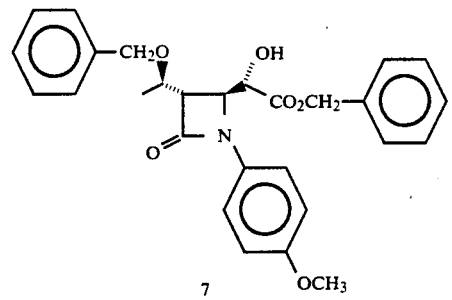

Compound 6 (438 mg: 1.136 mmol) was dissolved in 7 ml of anhydrous DMF, and 0.475 ml (3 equivalents) of triethylamine and 0.27 ml (2 equivalents) of benzyl bromide were added under ice cooling, followed by stirring overnight at room temperature. To the solution was added 150 ml of ethyl acetate. The resulting mixture was washed with a saturated sodium chloride aqueous solution, dehydrated with anhydrous sodium sulfate, and concentrated to dryness under reduced pressure.

The residue was purified by silica gel column chromatography (Merck Art 7734, (1) toluene, (2) toluene/ethyl acetate=10:1, (3) toluene/ethyl acetate=5:1) to afford 430 mg of the captioned compound (yield 79.6%).

IR(CHCl$_3$); 1730 cm$^-$($\beta$-lactam C=O), 1510 cm$^{-1}$(p-methoxyphenyl).

NMR(CDCl$_3$)$\delta$(PPM): 1.17(3H, d, J=6.1 Hz, CH$_3$), 3.38(2H, m, OH-5, CH-3), 3.77(3H, s, OCH$_3$), 3.9(1H, m, CH-7),

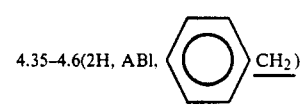
4.35–4.6(2H, ABl, 4.7(1H, dd, J=2.4 Hz, 5.0 Hz, CH-5), 5.0(2H, ABtype q, CH$_2$)

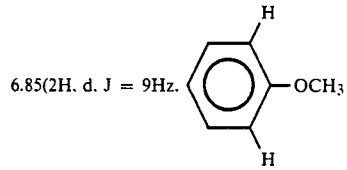
6.85(2H, d, J = 9Hz.

7.2–7.5(12H, m,

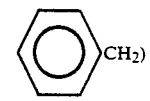

EXAMPLE 7

Synthesis of 3S,4S)-3-[(1R)-1-benzyloxyethyl]-4-[1-chloro-1-benztyloxycarbonyl]methyl-1-(4-methoxy)phenyl-2-azetidinone 8

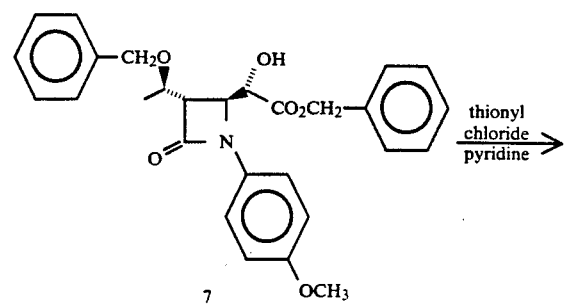
thionyl chloride pyridine

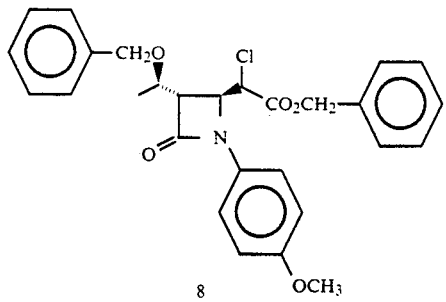

8

Compound 7 (102 mg: 0.2145 mmol) was dissolved in 2 ml of pyridine and 50 microliters (0.6854 mmol) of thionyl chloride were added under ice cooling, followed by stirring overnight at room temperature. The solution was poured into 20 ml of ice water, and extraction was conducted with 75 ml of ethyl acetate. The extract was washed with 50 ml of 0.5 N HCl and then with a saturated sodium chloride aqueous solution, a saturated NAHCO3 aqueous solution and a saturated sodium chloride aqueous solution in sequence. The organic layer was dehydrated with anhydrous Na2SO4, and concentrated to dryness under reduced pressure.

The residue was purified by silica gel column chromatography (Merck Art 7734, (1) toluene, (2) toluene/ethyl acetate=5:2) to obtain 92.5 mg of the captioned compound (yeild 87.4%).

IR(CHCl3); 1750 cm$^{-1}$($\beta$-lactam C=O), 1510 cm$^{-1}$(p-methoxyphenyl).

NMR(CDCl3)$\delta$(PPM): 1.37(3H, d, J=6.1 Hz, CH3), 3.47(1H, dd, J2.1 Hz, 5.1 Hz, CH-3), 3.77(3H, s, OCH3), 4.0(1H, m, CH-7),

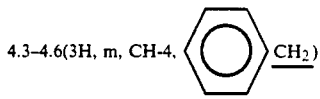

4.3–4.6(3H, m, CH-4, 4.78(1H, d, J=4.4 Hz, CH-5)

5.07(2H, s, <image (CH2)>

6.79(2H, d, J=9Hz, <image OCH3>

7.1–7.4(12H, m, 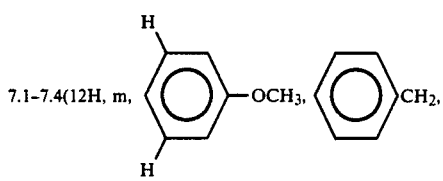

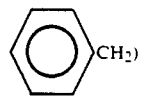

EXAMPLE 8

Synthesis of (3S,4R)-3-[(1R)-1-benzyloxyethyl]-4-(1-benzyloxycarbonyl)methyl)-1-(4-methoxy)phenyl-2-azetidinone 9

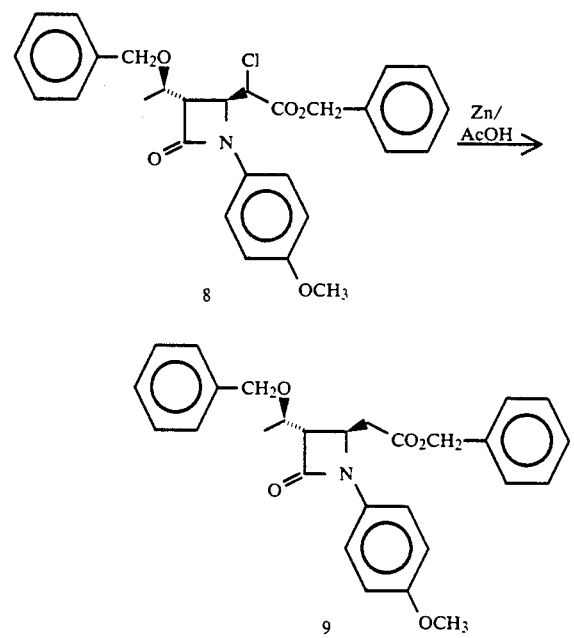

Compound 8 (89 mg: 0.1802 mmol) was dissolved in 5 ml of acetic acid, and 890 mg of zinc powder was added, followed by stirring at room temperature for 3.5 hours.

The reaction mixture was diluted with 50 ml of ethyl acetate and filtered through celite. The filtrate was washed with a 5% NaCO3 aqueous solution and a saturated sodium chloride aqueous solution, dehydrated with anhydrous sodium sulfate and then concentrated to dryness under reduced pressure.

The residue was purified by silica gel column chromatography (Merck Art 7734, (1) toluene, (2) toluene:ethyl acetate=10:1) to afford 73.2 mg of the captioned compound (yield 88.4%). matography (Merck Art (7734, (1) toluene, (2) toluene/ethyl acetate=10:1, (3toluene/ethyl acetate=5:1) to afford 430 mg of the captioned compound (yield 79.6%)

IR(CHCl3); 1750 cm$^{-1}$($\beta$-lactam C=O), 1510 cm$^{-1}$(p-methoxyphenyl).

NMR(CDCl3)$\delta$(PPM): 1.29(3H, d, J=6.1 Hz, CH3) 2.5–3.1(2H, m, CH2-5) 3.2(1), dd, J=2.4, 6.1 Hz, CH-3) 3.80(3H, s, OCH3)

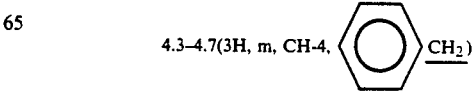

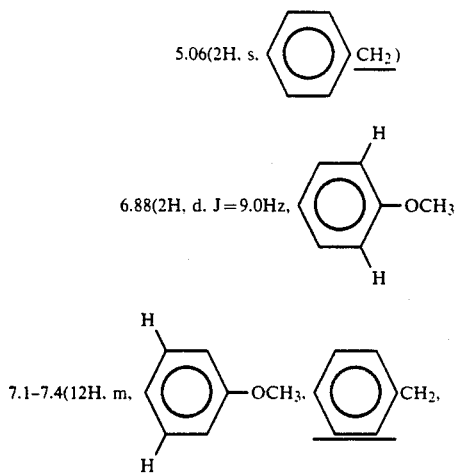

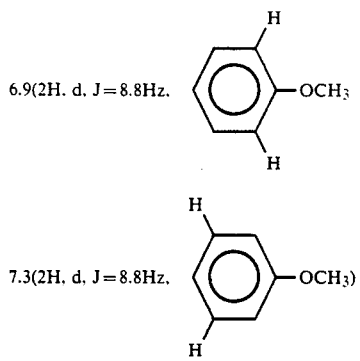

CH-3), 3.77(3H, s, OCH₃), 4.1(1H, m, CH-7), 4.4(1H, m, CH-4)

EXAMPLE 9

Synthesis of (3S,4R)-3-[(1R)-1-hydroxyethyl]-4-carboxymethyl-1-(4-methoxy)phenyl-2-azetidinone 10

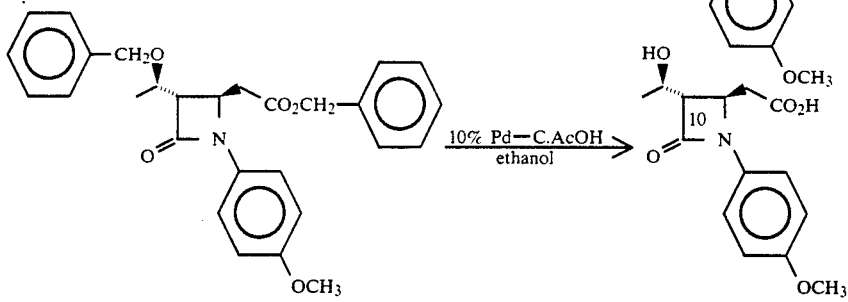

Compound 9 (370 mg: 0.8052 mmol) was dissolved in 20 ml of ethanol, and 0.925 ml of acetic acid and 370 mg of 10% palladium-carbon were added, followed by shaking for 24 hours under hydrogen pressure of 4.5 atm. The catalyst was filtered through celite and throughly washed with ethanol. The filtrate and the washing were together concentrated to dryness.

The residue was dissolved in 150 ml of a 0.1 N sodium hydroxide aqueous solution, and the solution was washed with 150 ml and 100 ml of dichloromethane. The aqueous layer was adjusted to pH of 2.5 with 1 N hydrochloric acid, and extracted with 200 ml and 100 ml of ethyl acetate. The organic layer was washed with 50 ml of a saturated sodium chloride aqueous solution, dehydrated with anhydrous sodium sulfate and concentrated to dryness under reduced pressure to obtain 188 mg of the captioned compound (yield 88.0%).

White crystal. m.p.: 145°-148° C.

IR(CHCl₃); 1720 cm⁻¹(β-lactam C=O), 1680 cm⁻¹(carboxylic acid C=O), 1510 cm⁻¹(p-methoxyphenyl).

NMR(CDCl₃)δ(PPM): 130(3H, d, J=6.6 Hz, CH₃), 2.6.-3.1(2H, m, CH₂-5), 3.15(1H, dd, J=2.2, 5.9 Hz,

EXAMPLE 10

Synthesis of (3S,4R)-3-[(1R)-1-hydroxyethyl]-4-(3p-nitrobenzyloxycarbonyl-2-oxo)propyl-1-(4-methoxy)phenyl-2-azetidinone 11

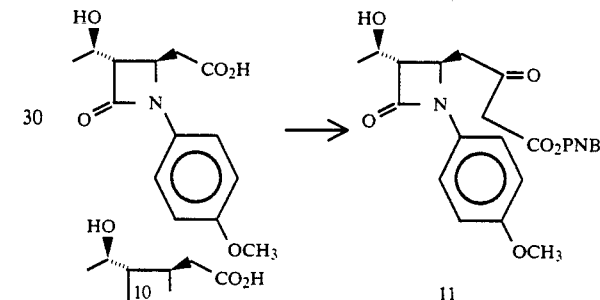

Compound 10 (98 mg: 0.3694 mmol) was dissolved in 3 ml of anhydrous THF, and 66 mg (0.407 mmol) of carbonyldiimidazole was added, followed by stirring at room temperature for 1 hour. Subsequently, 296 mg (0.5912 mmol) of magnesium p-nitrobenzyl malonate was added, and stirring was further conducted at room temperature for 20 hours.

The reaction mixture was diluted with 30 ml of ethyl acetate, and washed with 0.5 N hydrochloric acid, a saturated sodium chloride aqueous solution, a saturated NaHCO₃ aqueous solution and a saturated sodium chloride aqueous solution in sequence.

The organic layer was dehydrated with anhydrous sodium sulfate and then concentrated to dryness under reduced pressure.

The residue was purified by silica gel column chromatography (Merck Art 7734, toluene/acetone=5:1) to obtain 77 mg of the captioned compound (yield 45.7%).

IR(CHCl₃); 1735 cm⁻¹(β-lactam C=O), 1510 cm⁻¹(p-methoxyphenyl). 1340 cm⁻¹(nitro).

NMR(CDCl₃)δ(PPM): 1.33(3H, d, J=6.2 Hz, CH₃), −3.0-(3H, m, CH₂-5, CH-3), 3.6(2H, s, CH₂-7), 3.8(3H, s, OCH₃) 4.0–4.5(2H, m, CH-4, CH-9),

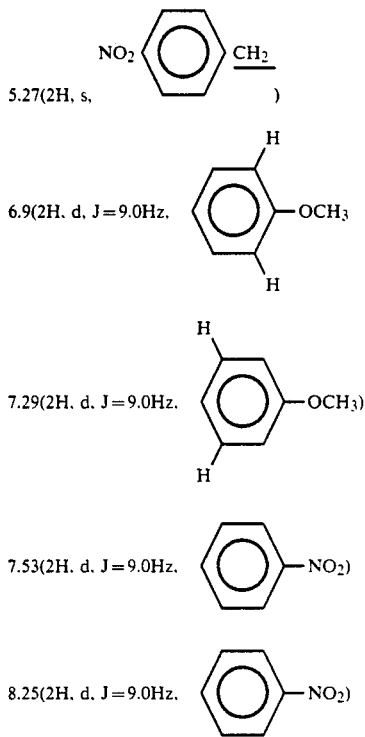

EXAMPLE 11

Synthesis of (3S,4R)-3-[(1R)-1-hydroxyethyl]-4-[3-p-nitrobenzyloxycarbonyl-2-oxo-]propyl-2-azetidone 12

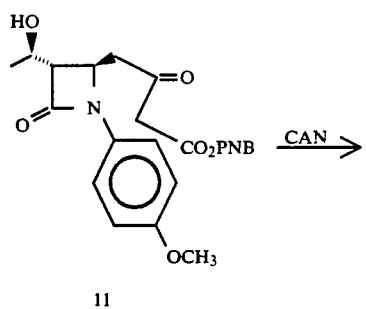

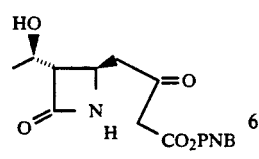

Compound 11 (24 mg: 0.0526 mmol) was dissolved in 2 ml of acetonirile, and a solution of 57.6 mg (0.105 mmol) of ceric ammonium nitrate in 1 ml of water was added dropwise at −5° C. After the addition, the mixture was stirred at −5° C. for 1 hour, and extracted with the addition of 40 ml of ethyl acetate and 20 ml of a saturated NaOHCO₃ aqueous solution. The aqueous layer was extracted with a small amount of ethyl acetate and combined with the above organic layer. The organic layer was washed with a 5% sodium thiosulfate aqueous solution, a saturated NaHCO₃ aqueous solution and a saturated sodium chloride aqueous solution in sequence. The resulting product was dehydrated with anhydrous sodium sulfate, and then concentrated to dryness under reduced pressure. The residue was purified by silica gel column chromatography (Merck Art 7734, (1) toluene/ethyl actetate=1:1, (2) toluene/acetone=2:1, (3) toluene/acetone=1:1, (4) toluene/acetone=1:3) to obtain 12 mg of the captioned compound (yield 65%).

IR(CHCl₃); 1750 cm⁻¹(β-lactam C=O), 1705 cm⁻(C=O), 1505, 1340 cm⁻¹(niro).

NMR(CDCl₃)δ(PPM): 1.3(3H, d, J=6.2 Hz, CH₃), 2.7-3.1(3H, m, CH₂-5, CH-3), 3.60(2H, s, CH₂-7) 3.8-4.3(2H, m, CH-4, CH-9,

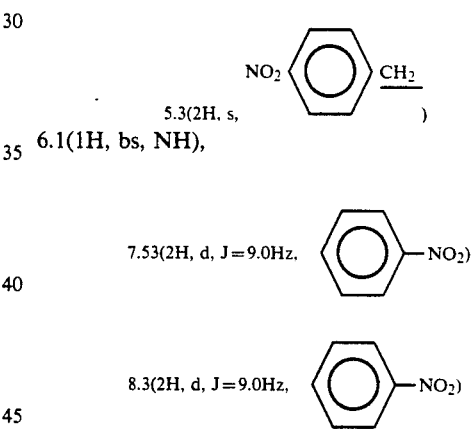

EXAMPLE 12

Synthesis of (3S,4S)-3-[(1R)-1-benzykloxyethyl]-4-(1-chloro-1-chlorocarbonyl)methyl-1-(4-methoxy)phenyl-2-azetidinone 13

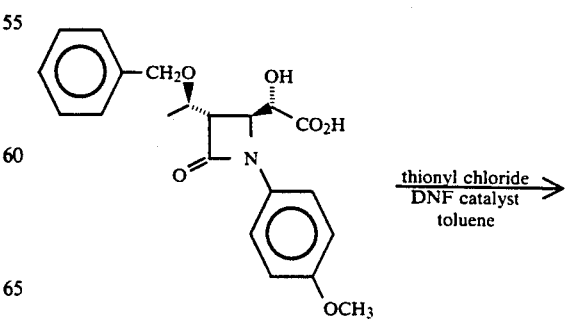

-continued

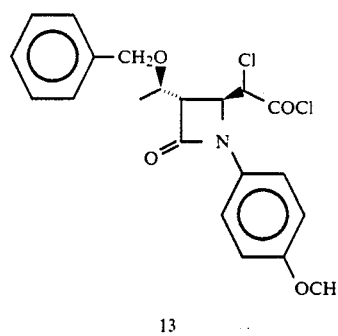

13

One hundred milligrams (0.2595 mmol) of compound 6 was suspended in 2 ml of anhydrous toluene, and 130 microliters (1.782 mmols) of thionyl chloride and 19.6 microliters (0.253 mmol) of anhydrous DMF were added, followed by stirring at 70° C. for 1 hour.

The reaction mixture was concentrated to dryness under reduced pressure to obtain the captioned compound.

IR(CHCl$_3$); 1750 cm$^{-1}$($\beta$-lactam C=O), 1510 cm$^{-1}$(p-methoxyphenyl).

NMR(CDCl$_3$)$\delta$(PPM): 1.38(3H, d, J=6.3 Hz, CH$_3$), 3.4(1H, dd, J=2.0, 5.0 Hz, CH-3), 3.8(3H, s, CH$_3$), 3.9–4.2(1H, m, CH-7),

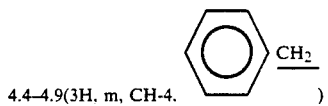

4.4–4.9(3H, m, CH-4, 5.0(1H, d, J=3 Hz, CH-5),

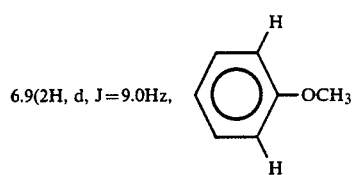

6.9(2H, d, J=9.0Hz,

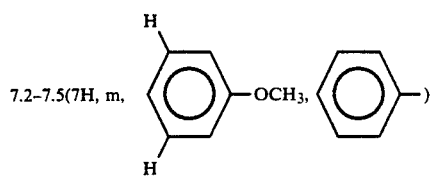

7.2–7.5(7H, m,

EXAMPLE 13

Synthesis of (3S,4R)-3-[(1R(-1-benzyloxyethyl]-4-carboxymethyl-1-(4-methoxy)phenyl-2-azetidinone 14

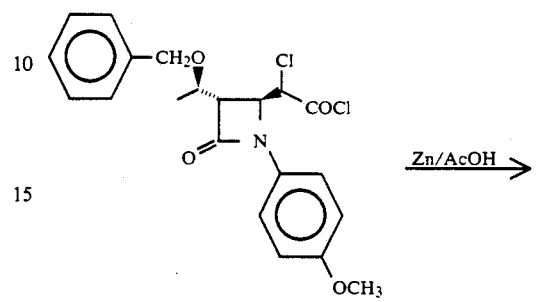

13

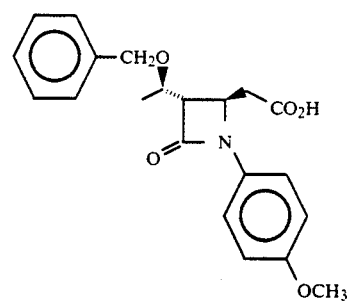

14

The compound 13 obtained in Example 12 was dissolved in 4 ml of acetic acid, and 500 mg of zinc powder was added thereto, followed by stirring overnight at room temperature. The reaction mixture was filtered through celite, and concentrated to dryness under reduced pressure.

The residue was dissolved in 20 ml of ethyl acetate, and extraction was carried out with a cold 0.5 N sodium hydroxide solution. The aqueous layer was washed with 20 ml of ethyl acetate, adjusted to pH of 2.5 with 1 N hydrochloric acid and extracted with 30 ml and 10 ml of ethyl acetate.

The aqueous layer was washed with a saturated sodium chloride aqueous solution, then dehydrated with anhydrous sodium sulfate, and concentrated to dryness under reduced pressure to obtain 68 mg of the captioned compound.

IR(CHCl$_3$); 1750 cm$^{-1}$($\beta$-lactam C=O), 1510 cm$^{-1}$(p-methoxyphenyl).

NMR(CDCl$_3$)$\delta$(PPM): 1.3(3H, d, J=6.1 Hz, CH$_3$), 2.5–3.0(2H, m, CH$_2$-5), 3.2(b 1H, dd, J=2.1, 5.1 Hz, CH-3), 3.8(3H, s, CH$_3$), 3.9–4.2(1H, m, CH-7), 3.9–4.2(1H, m, CH-7)

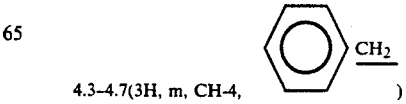

4.3–4.7(3H, m, CH-4,

-continued 6.9(2H. d. J=9.0Hz. 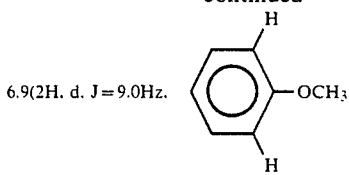

7.2-7.5(7H. m.  )

8.5(1H, bs, COOH.

EXAMPLE 14

Synthesis of (3S,4S)-3-[(1R(-1-benzyloxyethyl]-4-(1-chloro-1-methoxycarbonyl)methyl-1-(4-methoxy)phenyl-2-azetidinone 16

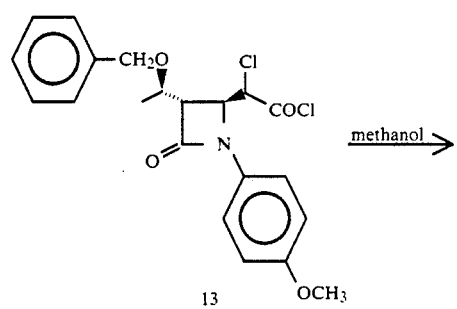

methanol →

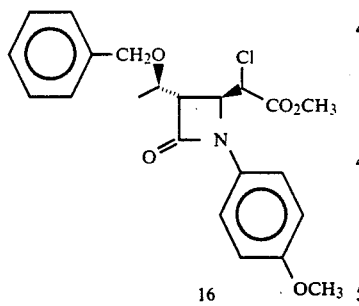

Compound 13 synthesized in accordance with the process in Example 12 was dissolved in 1 ml of anhydrous methanol, and stirred at room temperature for 3 hours. To the reaction solution was added ethyl acetate, and the mixture was washed twice with a saturated sodium chloride aqueous solution. The organic layer was dehydrated with anhydrous sodium sulfate, and then concentrated to dryness under reduced pressure. The residue was purified by silica gel column chromatography (Merck Art 7734, (1) toluene, (2) toluene/ethyl acetate=10:1) to provide 61 mg of the captioned compound.

IR(CHCl$_3$); 1750 cm$^{-1}$(β-lactam C=O), 1510 cm$^{-1}$(p-methoxyphenyl).

NMR(CDCl$_3$)δ(PPM): 1.35(3H, d, J=6.1 Hz, CH$_3$), 3.45(1H, dd, J=6.0 Hz, 2.2 Hz, CH-3),

3.68(3H. s. COCH$_3$)

3.80(3H, s, OCH$_3$), 3.9-4.2(1H, m, CH-7), 4.4-4.8(4H, m, CH-4, 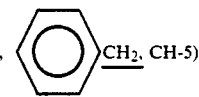 CH$_2$, CH-5)

6.88(2H, d, J=9.0Hz. 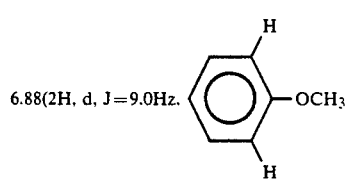

7.2-7.4(7H. m. 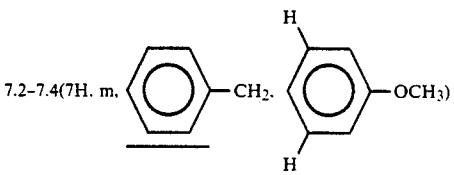 )

EXAMPLE 15

Synthesis of (3S,4R)-3-[(1R)-1-benzyloxyethyl]-4-(1-methoxycarbonyl)methyl-1-(4-methoxy)phenyl-2-azetidinone 18

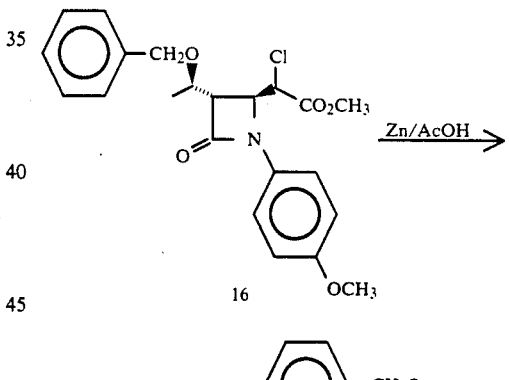

Zn/AcOH →

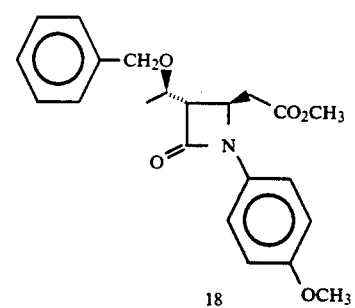

Compound 16 (61 mg: 0.146 mmol) was dissolved in 2 ml of acetic acid, and 200 mg of zinc powder was added, followed by stirring at room temperature.

After stirring for 6.5 hours, the mixture was diluted with ethyl acetate and filtered. The filtrate was washed twice with a saturated NaHCO$_3$ aqueous solution and once with a saturated sodium chloride aqueous solution. The organic layer was dehydrated with anhydrous sodium sulfate, and then concentrated to dryness under reduced pressure. The residue was purified by silica gel column chromatography (Merck Art (7734, (1) toluene, (2) toluene/ethyl acetate=10:1) to provide 50 mg of the captioned compound.

IR(CHCl₃); 1730 cm⁻¹(β-lactam C=0), 1510 cm⁻¹(p-methoxyphenyl).

NMR(CDCl₃)δ(PPM): 1.33(3H, d, J=6.1 Hz, CH₃), 2.5-3.3(3H, m, CH-3, CH₂-5),

3.65(3H, s, COCH₃)

3.82(3H, s, OCH₃) 3.8-4.1(1H, m, CH-7),

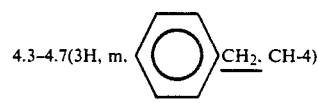
4.3-4.7(3H, m, ⌬CH₂, CH-4)

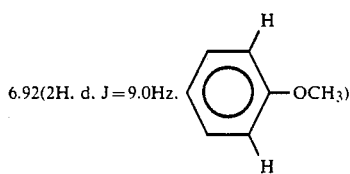
6.92(2H, d. J=9.0Hz. ⌬-OCH₃)

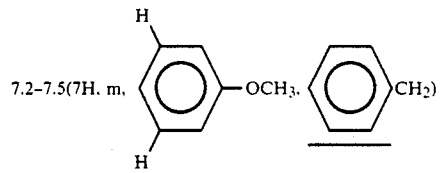
7.2-7.5(7H, m, ⌬-OCH₃, ⌬CH₂)

EXAMPLE 16

Synthesis of (3S,4S)-3-[(1R)-1-benzyloxyethyl]-4-[1-chloro-1-phenylthiocarbonyl]methyl-1-(4-methoxy)phenyl-2-azetidinone 15

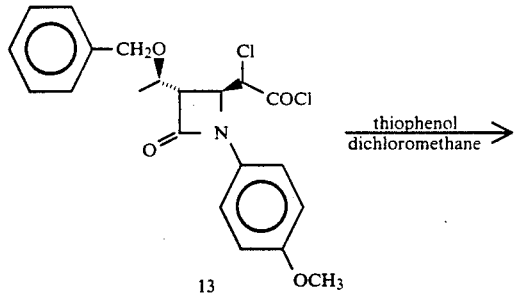

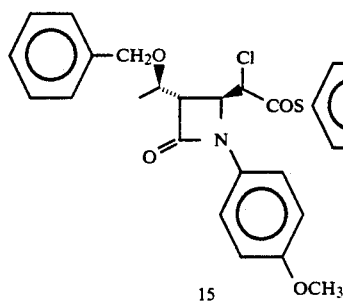

Compound 13 synthesized in accordance with the process in Example 12 was dissolved in 2 ml of anhydrous dichloromethane,. With stirring, b 30 microliters (0.292 mmol) of thiophenol was added at −5° C.

One hour later, 50 microliters of thiophenol was further added and the mixture was stirred for 1 hour. The silution liquid was diluted with ethyl acetate, and washed with a saturated NaHCO₃ aqueous solution and a saturated sodium chloride aqueous solution. The organic layer was dehydrated with anhydrous sodium sulfate, and concentrated to dryness under reduced pressure.

The residue was purified by silica gel column chromatography (Merck Art 7734, (1) toluene, (2) toluene/ethyl acetate=10:1) to obtain 19 mg of the captioned compound as an oil.

IR(CHCl₃); 1750 cm⁻¹(β-lactam C=0), 1510 cm⁻¹(p-methoxyphenyl). 1680 cm⁻¹(ester C=0).

NMR(CDCl₃)δ(PPM): 1.28(3H, d, J=6.1 Hz, CH₃), 3.81(3H, s, OCH₃/), 3.9-4.2(1H, m, CH-7),

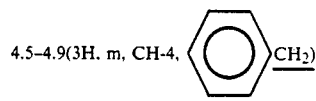
4.5-4.9(3H, m, CH-4, ⌬CH₂)

5.06(1H, d, J=3.0 Hz, CH-5),

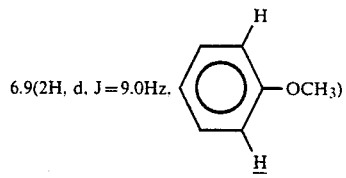
6.9(2H, d, J=9.0Hz. ⌬-OCH₃)

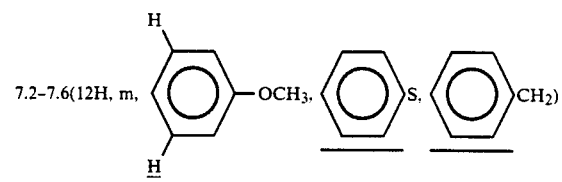
7.2-7.6(12H, m, ⌬-OCH₃, ⌬S, ⌬CH₂)

EXAMPLE 17

Synthesis of (3S,4R)-3-[(1R)-1-benzyloxyethyl]-4-(1-phenylthiocarbonyl)methyl-1-(4-methoxy)phenyl-2-azetidinone 17

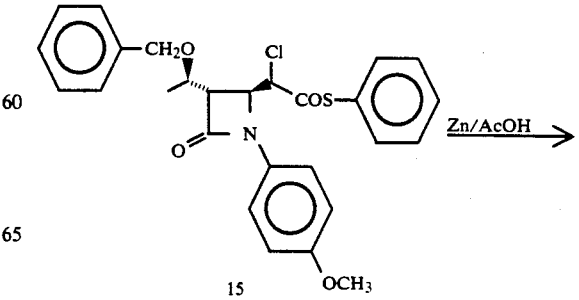

-continued

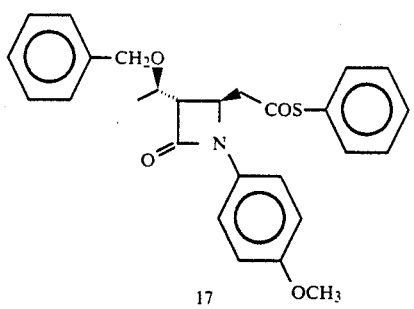

Compound 15 (19 mg: 0.383 mmol) was dissolved in 1 ml of acetic acid, and 100 mg of zince powder was added, followed by stirring at room temperature. After 3.5 hours, 60 mg of zinc powder was added, and stirring was then conducted for 1 hour.

To the reaction mixture was added ethyl acetate, and filtration was conducted. The filtrate was washed twice with a saturated $NaHCO_3$ aqueous solution and once with a saturated sodium chloride aqueous solution. The aqueous layer was dehydrated with anhydrous sodium sulfate, and then concentrated to dryness under reduced pressure. The residue was purified by silica gel column chromatography (Merck Art 7734, (1) toluene, (2) toluene;ethyl acetate=10:1) to obtain 9 mg of the captioned compound.

IR($CHCl_3$); 1735 $cm^{-1}$($\beta$-lactam C=O), 1690 $cm^{-1}$(ester C=O), 1510 $cm^{-1}$(p-methoxyphenyl).

NMR($CDCl_3$)$\delta$(PPM): 1.33(3H, m, CH-3, $CH_2$-5), 2.8–3.4(3H, m, CH-3, $CH_2$-5), 3.84(3H, s, $OCH_3$), 3.85–4.2(1H, m, CH-7),

5.06(1H, d, J=3.0 Hz, CH-5)

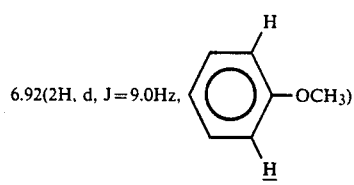

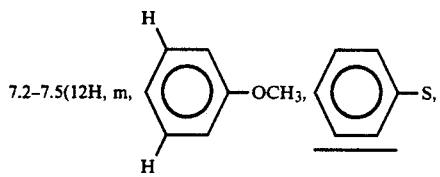

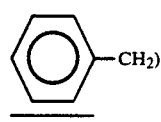

EXAMPLE 18

Synthesis of (3S,4R)-3-[(1R)-1-hydroxyethyl]-4-carboxymethyl-1-(4-methoxy)phenyl-2-azetidinone 10

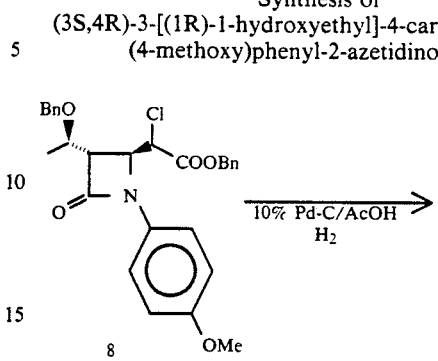

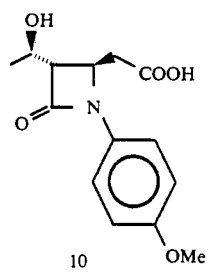

Compound 8 (22.9 mg: 0.0464 mmol) was dissolved in 0.5 ml of acetic acid, and 23.9 mg of 10% Pd-C was added, followed by stirring for 22 hours under an atmosphere of hydrogen. Further, 14.2 mg of 10% Pd-C was added, and the stirring was conducted run for 4 hours under an atmosphere of hydrogen. The reaction mixture was then diluted with ethanol and filtered through celite. The filtered product was thoroughly washed with ethanol, and the filtrate and the washing were together diluted with toluene and concentrated to dryness under reduced pressure. The same procedure was conducted twice to afford 12.8 mg of the captioned compound (yield 87.4%).

What we claim is:

1. A compound of the formula:

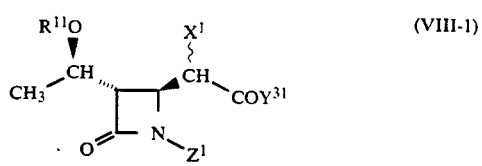

wherein
$R^{11}$ denotes a lower alkanoyl group, a halo-lower alkanoyl group, an allyl group, a benzyloxycarbonyl group, a p-nirobenzyloxycarbonyl group or a p-chlorobenzyloxycarbonyl group; $X^1$ denotes a chlorine or bromine atom; $Y^{31}$ denotes a chlorine or bromine atom, an -S-lower alkyl group or an -S-phenyl group; and $Z^1$ denotes a hydrogen atom, a phenyl group, a 4-methoxyphenyl group, a 2,4-dimethoxyphenyl group, a benzyl group, a p-nitrobenzyl group, a dianisylmethyl group of a 2,4-dimethoxybenzyl group.

* * * * *